United States Patent [19]

Phillips

[11] Patent Number: 5,028,143
[45] Date of Patent: Jul. 2, 1991

[54] HUMIDITY DEW POINT SENSOR

[76] Inventor: David E. Phillips, P.O. Box 709, Harve de Grace, Md. 21078-0709

[21] Appl. No.: 610,654

[22] Filed: Nov. 8, 1990

Related U.S. Application Data

[63] Continuation-in-part of Ser. No. 429,742, Oct. 31, 1989, abandoned.

[51] Int. Cl.$^5$ .................. G01N 25/68; G01N 25/66
[52] U.S. Cl. ..................... 374/15; 374/20; 374/18
[58] Field of Search .................. 374/16, 17, 18, 19, 374/20, 27, 28, 15

[56] References Cited

U.S. PATENT DOCUMENTS

| | | | |
|---|---|---|---|
| 2,336,238 | 12/1943 | Fordyce et al. | 374/15 |
| 3,589,169 | 6/1971 | Lafitte et al. | 374/15 |
| 3,597,084 | 8/1971 | Pagano | 374/15 |
| 3,623,356 | 11/1971 | Bisberg | 374/20 |
| 3,869,912 | 3/1975 | Horvath | 374/15 |
| 3,875,794 | 4/1975 | Horvath | 374/15 |
| 4,276,768 | 7/1981 | Dadachanji | 374/28 |
| 4,629,333 | 12/1986 | Dosoretz et al. | 374/20 |

FOREIGN PATENT DOCUMENTS

| | | | |
|---|---|---|---|
| 3432261 | 4/1985 | Fed. Rep. of Germany | 374/15 |
| 1299662 | 6/1962 | France | 374/15 |
| 0645069 | 1/1979 | U.S.S.R. | 374/20 |
| 0813208 | 3/1981 | U.S.S.R. | 374/28 |

Primary Examiner—William A. Cuchlinski, Jr.
Assistant Examiner—Diego F. F. Gutierrez
Attorney, Agent, or Firm—Saul Elbaum; Guy M. Miller; Paul S. Clohan

[57] ABSTRACT

An elongated mirrored surface has a temperature gradient established thereacross. Condensation forms along the mirrored surface and the edge of the condensation next to the portion of the mirrored without condensation is where the dew point temperature exists. A scanning means is provided for locating this edge of the condensation. Temperature sensing means, located at the edge, measures the dew point temperature.

10 Claims, 3 Drawing Sheets

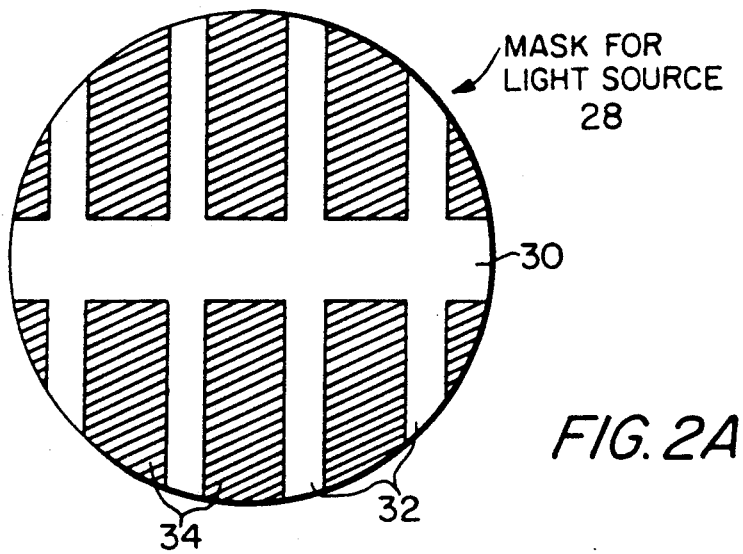
FIG. 2A
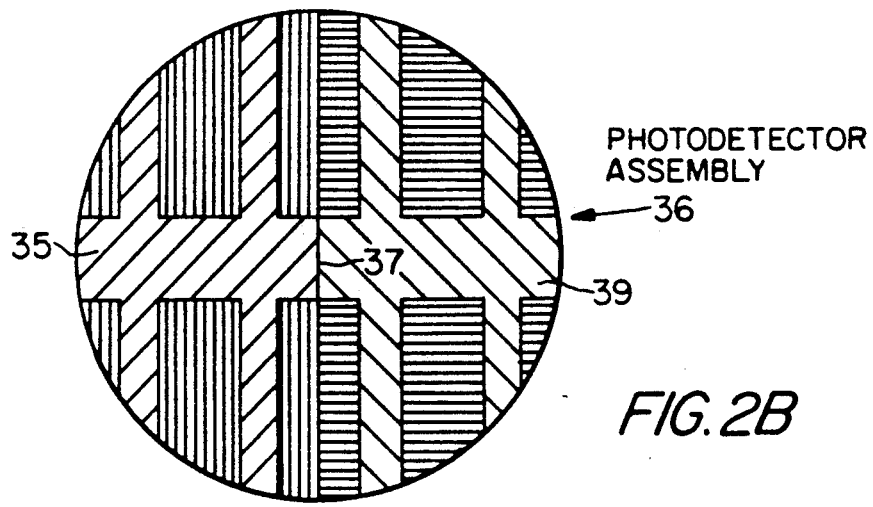
FIG. 2B
FOUR REGIONS OF PHOTODETECTOR ASSEMBLY
FIG. 2C
 = REGION 1
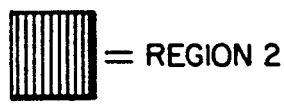 = REGION 2
 = REGION 3
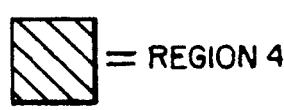 = REGION 4

HUMIDITY DEW POINT SENSOR

RIGHTS OF THE GOVERNMENT

The invention described herein may be manufactured, used and licensed by or for the United States Government for Governmental Purposes without payment to me of any royalty thereon.

This application is a continuation-in-part of my earlier filed application, Ser. No. 07/429,742, filed 10/31/89, now abandoned.

BACKGROUND OF THE INVENTION

The present invention relates to apparatus for measuring humidity (dew point).

Various forms of apparatus are known for measuring the dew point, including electrically operated apparatus arranged to affect at least part of the measuring process automatically. Known dew point measuring apparatus of the last-noted type generally operate by one of two methods.

In the first such method, a body having an optically smooth surface is kept continuously at the dew point by means of a thermo-electric cooling means controlled by a signal derived from a light-sensitive element such as a photocell arranged to detect the scattering from the smooth surface of light from a light beam directed onto said surface, the scattering resulting from the formation of dew on the surface. The arrangement is such that the amount of dew on the surface is maintained at a substantially constant predetermined level by corresponding regulation of the temperature so that the temperature of the surface is maintained continuously at the dew point.

In a second method, a body having an optically smooth surface is cooled thermo-electrically from a temperature above the dew point, the temperature of the surface being monitored continuously. A beam of light is directed onto the surface and the formation of dew thereon is again detected by the consequent scattering of light from the surface. The temperature at which the degree of such scattering reaches a predetermined level is taken as a measure of the dew point temperature. Where continuous monitoring of the dew point is required, the body providing the optically smooth surface is allowed to rise above the dew point temperature each time it has been cooled below this temperature and the cycle is repeated continuously so that the dew point temperature is effectively sampled at regular intervals.

In the first-noted method, continuous monitoring of the dew point temperature is provided automatically.

The first of the two methods noted has the disadvantage of requiring more power than the second method (this power being required to maintain the body providing the smooth surface continuously at a low temperature), the dissipation of this power giving rise inevitably to the generation of heat elsewhere in the apparatus, and thus at a location fairly close to the body being cooled. This circumstance may give rise to errors unless one resorts to complex ventilation arrangements to achieve thermal equilibrium.

The second of the two methods discussed affords the inherent disadvantage that the frequency at which samples of dew point temperature are provided is lower the higher the accuracy required since, if the earliest possible detection of dew formation on the surface is to be achieved and errors due to time lag effects are to be avoided, it is necessary for the body providing the optically smooth surface to be cooled very slowly so that the duration of each sampling interval is correspondingly long and the sampling frequency correspondingly low.

An improvement of the second-noted method is disclosed in U.S Pat. No. 4,276,768 which provides an apparatus for measuring the dew point. The apparatus comprises a body having associated therewith means for sensing the formation of dew on the body, means for cooling the body, and means for sensing the temperature of the body. The apparatus further comprises control means arranged to cause the apparatus to perform a cycle repeatedly in which the body is cooled gradually until the formation of dew thereon is detected. A temperature at which dew forms on the body is recorded in the apparatus and the temperature of the body being subsequently allowed to rise prior to cooling again in the next succeeding cycle. The temperature of the body is monitored continuously and the rate of cooling of the body is controlled in dependence upon the difference between the instantaneous temperature of the body and the dew point temperature measured in a preceding cycle and recorded in the apparatus, in such a way that the rate of cooling is lower for at least a range of temperatures closer to the dew point temperature recorded in the previous cycle than for instantaneous temperatures of the body further from the dew point temperature recorded in the previous cycle. Thus, it is possible to combine the advantages of a rapid cooling rate, affording a high sampling frequency, and of a slow cooling rate, affording good accuracy.

Utilization of the improved prior art approach permits accurate measurement of the dew point temperature, thereby allowing one to calculate relative and/or absolute humidity if the air temperature is known. The problem of this prior art is that, when the temperature and humidity are changing rapidly, as in an environmental simulation chamber, the temperature cycle of the mirrored surface can go out of control. The purpose of the present invention is to solve that problem.

BRIEF DESCRIPTION OF THE PRESENT INVENTION

A mirrored internal cylindrical surface has a temperature gradient imposed on it such that a portion (approximately half) is at a temperature above the dew point and a portion (the other half) is at a temperature below the dew point. A light source and one or more light detectors are used to locate the edge of clouding, where water vapor just begins to condense on the mirrored surface. The temperature of two thermoelectric coolers are automatically adjusted so that the mirrored surface is half clear and half clouded by condensed water vapor. The dew point will then be half-way between the temperature of the two thermoelectric coolers.

BRIEF DESCRIPTION OF THE DRAWINGS

FIG. 2A is a plan view of a mask for a light source which has opaque areas to define a number of light source regions.

FIG. 2B is a plan view of a photodetector assembly having a number of image regions defined thereon.

FIG. 2C illustrates the cross hatch representations of the four image regions on the photodetector mask of FIG. 2B.

DETAILED DESCRIPTION OF THE INVENTION

Figure 1:
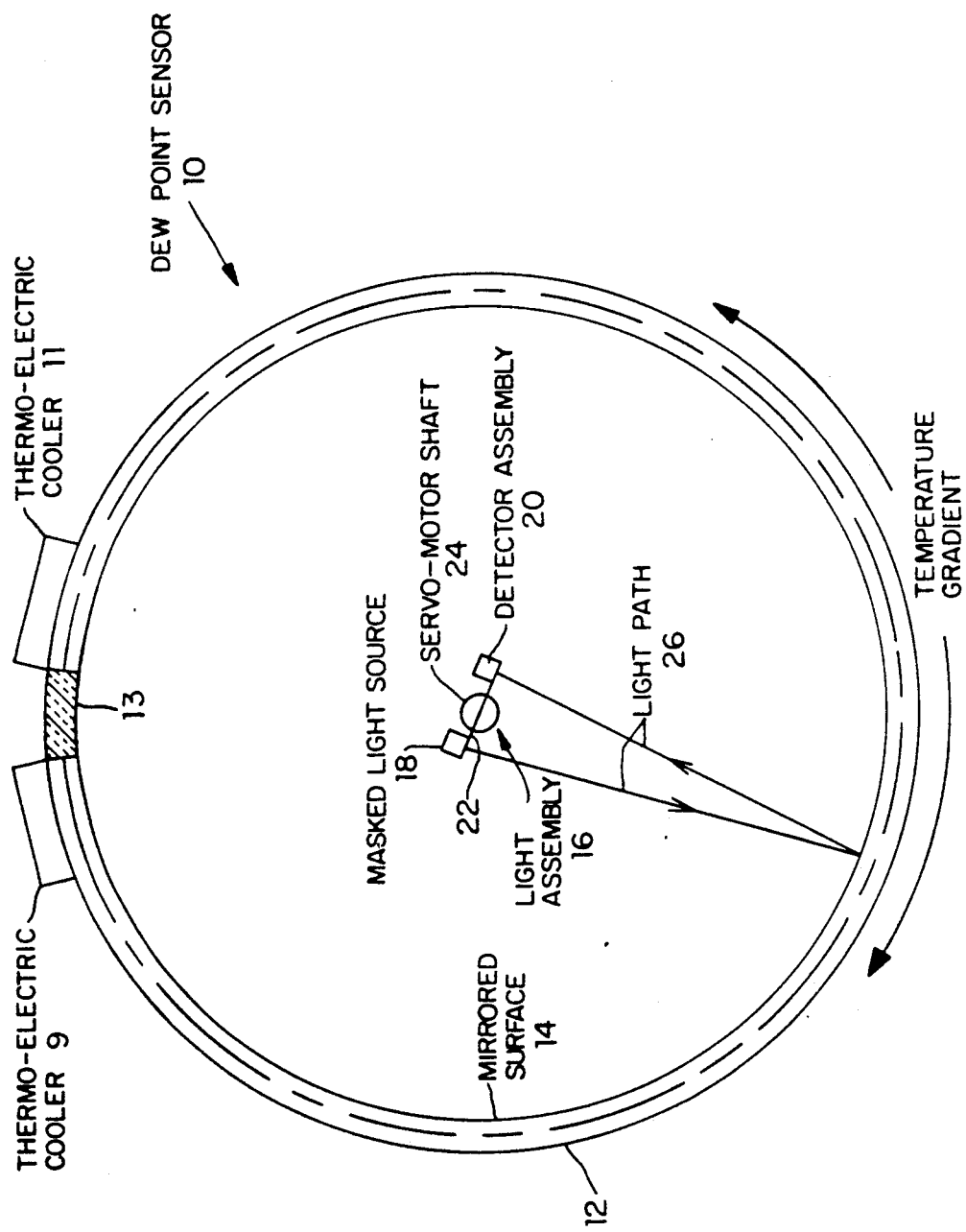
FIG. 1 is a schematic representation of the present invention.

FIG. 1 illustrates the basic dew point sensor 10 of the invention. A hollow cylindrical body 12, has its inside surface 14 mirrored. Two thermo-electric coolers 9 and 11 are intimately attached to body 12 and separated from each other by thermal insulator 13, which runs along an elongated gap or opening of body 12 and provides thermal isolation between the left and right halves of body 12. Thermo-electric coolers are well established in the prior art, as evidenced in U.S. Pat. No. 4,276,768. Thermo-electric coolers 9 and 11 are operated so that a well defined temperature gradient will exist between them along mirrored surface 14. The creation of a well-defined constant temperature gradient is well understood to one skilled in the art and is accomplished as follows: thermo-electric cooler 11 is used to cool body 12 down to a predetermined temperature (i.e., cooler 11 is "set" to a particular temperature) while thermo-electric cooler 9 is also used to cool down body 12 but not as much as thermo-electric cooler 11 (i.e., cooler 9 is "set" to a higher temperature than cooler 11). Thus, the right-hand portion of body 12 will be at a lower temperature than the left-hand portion of body 12 and therefore because the temperature of thermo-electric coolers 9 and 11 are known, a well-defined constant temperature gradient will exist along body 12 from it's right-hand portion to it's left hand portion. In other words, if body 12 has a cold area and a warmer area, the portion of the surface between the cold area and the warmer area will be neither cold nor warm but will have a temperature gradient from cold to warm. For example, if the left-hand part of body 12 were at 40° with the right-hand part of body 12 at 30° and the circumference of body 12 was 10 inches, then a well-defined constant temperature gradient from the left-hand part to the right hand part is 1° per inch, and the temperature at any point in-between will also be known (e.g., at four inches from thermo-electric cooler 9, the temperature must be 36°). This is an inherent characteristic of a surface subjected to two different thermal stresses, and is well understood in this art.

In order to determine the dew point, it is necessary that the dew point temperature be between the temperature of the two thermo-electric coolers 9 and 11 and therefore, exist at a point along mirrored surface 14. When the dew point is half-way between the temperature of the two thermo-electric coolers 9 and 11, half of the mirrored surface 14 will be clouded by condensed water vapor and the other half will be clear of condensation. If the dew point temperature is closer to the temperature of the cooler thermo-electric cooler (cooler 11), less of the mirrored surface will be clouded. Because the temperature gradient is linear the line separating the clouded and clear portions of the mirrored surface will be at a distance between the thermo-electric coolers proportional to the difference between the dew point and the temperature of the coolers.

In order to detect the edge of clouding, a light assembly 16 is employed. The assembly includes a masked light source 18 which is focused on the virtual image of the light assembly 16 on mirrored surface 14, impinging a multi-region masked light beam onto mirrored surface 14. Light assembly 16 also includes a detector assembly 20 which has four regions of sensitivity. Light assembly 16 is mounted on servo-motor shaft 24 which is located at the axial center of body 12, and mounts masked light source 18 along an extended diametrical support beam 22 with detector assembly 20 located on the opposite end of support beam 22. Masked light source 18 and detector assembly 20 are attached to servo-motor shaft 24 such that the image of the light mask will always be focused on detector assembly 20.

FIGS. 2A-2C illustrates a means for generating a masked light image along light path 26 (FIG. 1). The mask 28 illustrated in FIG. 2A is adapted to be positioned in front of the light source so that a patterned beam impinges upon the mirrored surface 14. The pattern for the mask includes a series of parallel spaced areas 32 intersected by a central transparent area 30. The result will be a number of intermediate opaque areas 34.

FIG. 2B illustrates a corresponding line pattern on a photodetector array assembly 36 which results from the masked light source 18. As will be observed in FIG. 2B, a generally circular photodetector surface is defined between two mating semicircular components 35 and 39 which meet along diametrical junction 37. FIG. 2C defines the unmasked light regions 1 and 4 which result from the unmasked light shining through transparent parallel spaced areas 30, 32. Diminished light regions will occur on the photodetector assembly 36 (FIG. 2B) as a result of the opaque areas 34 on the mask 28 (FIG. 2A) of the light source. These diminished light regions are defined as regions 2 and 3, respectively existing on opposite sides of the diametric junction 37.

Figure 3:
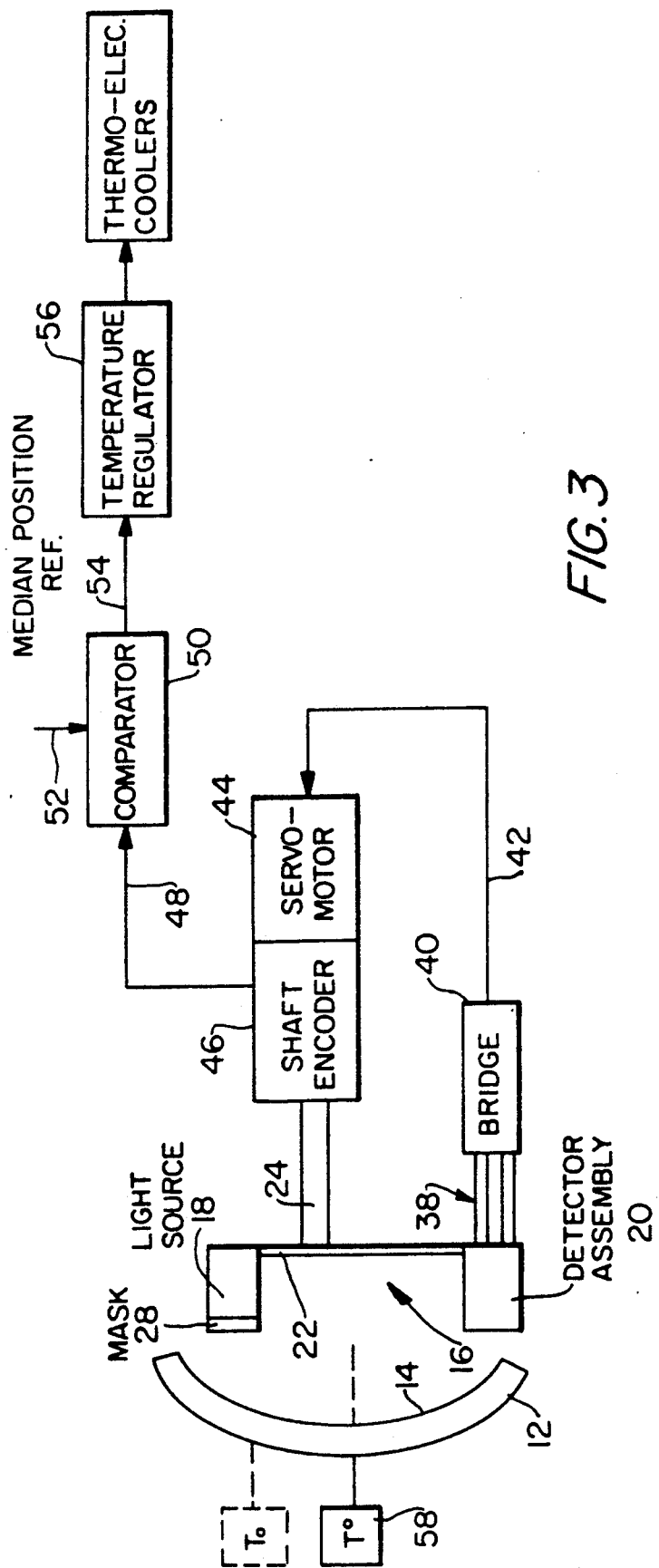
FIG. 3 is a simplified block diagram of the present inventive system.

A preferred system for accomplishing accurate positioning of light assembly 16 is illustrated in FIG. 3. The system in FIG. 3 includes a shaft encoder 46 or other angular position device, which is connected to shaft 24. The output 48 from the shaft encoder measures the angular position of the shaft at any moment in time. The shaft 24 is rotated by a conventional servo motor 44, which is driven from the output 42 of bridge 40, the latter having its inputs 38 connected to respective regions 1-4 of the detector assembly 20.

When mirrored surface 14 is clear, virtually all of the light will strike detector assembly 20 on regions 1 and 4. When mirrored surface 14 is clouded, the amount of light which reaches regions 2 and 3 will increase dramatically while the light which reaches regions 1 and 4 will decrease due to the scattering of light path 26 by clouded surface 14. When the virtual image of mask 28 is centered on the edge of clouding, the difference in the amount of light which reaches regions 1 and 2 will be maximized, while the difference in the amount of light which reaches regions 3 and 4 will be minimized.

In a typical operation of the device, an unbalanced bridge causes the servo motor 44 to rotate shaft 24 until reaching the center point where the dew point clouding has been detected. At this point, bridge 40 becomes balanced and the motion of shaft 24 stops. For example, if the outputs from regions 2 and 3 are the same and above the "dark" current threshold, the servo-motor shaft will be rotated toward the warmer end of body 12. If the outputs from regions 2 and 3 are the same and not above the "dark" current threshold, the servo-motor shaft will be rotated toward the cooler end of body 12. If the outputs from regions 2 and 3 are different, then a comparison of the differences between regions 1 and 2 and regions 3 and 4 is made; if the difference between the outputs from regions 1 and 2 is below a pre-set maximum, teen the servo-motor shaft will be rotated toward the warmer end of body 12; if the difference between the outputs from regions 3 and 4 is above a pre-set minimum, then the servo-motor shaft will be rotated toward the cooler end of body 12. A comparator 50 then makes a comparison between a reference signal 52 indicative of the median position along mirrored surface 14 and the actual signal from the shaft encoder output 48. If the comparator 50 determines that the position where the dew point clouding occurs is not at the median position along mirrored surface 14, it generates an output 54 to temperature regulator 56 for driving thermo-electric coolers 9 and 11 in a direction that would vary the temperature gradient across the mirrored surface 14. The gradient is varied until the dew point clouding is detected at the exact median position along the mirrored surface 14. The dew point temperature is then half-way between the temperature of the "warmer" thermo-electric cooler and the "cooler" thermo-electric cooler. Because the temperature of cooler 9 and cooler 11 is known, the dew-point temperature is also known. Alternatively, instead of calculating the dew-point temperature, a thermometer 58 can be used to establish the dew point temperature. Once the dew point is established, conventional calculations are followed to derive absolute and relative humidity.

Another form of the invention would exclude comparator 50 and the provision for variation of the temperature gradient across the mirrored surface so that dew point clouding occurs at the median position. Rather, a plurality of temperature-sensing devices 58 would sense the temperature at a large number of points on the temperature gradient and a read-out would be made from a temperature sensor where dew point clouding was detected. This is operationally achieved when shaft 24 stops after a dew point condition has been detected and the position of shaft encoder 46 is determined. The temperature sensor corresponding to the shaft encoder position is then read out thereby establishing the dew point temperature.

Another form of the invention would include more complex logic to change the temperature differential between thermo-electric coolers 9 and 11 depending on the rate of change of the dew point temperature. If the dew point was changing rapidly, the temperature differential would increase. If the dew point was changing slowly, the temperature differential would be adjusted downward, increasing accuracy.

As described above, the present invention provides an accurate way to measure dew point in a situation where environmental humidity is changing rapidly, as in the case of environmental simulation chambers. This invention allows test personnel to more accurately and reliably determine humidity in test chambers and to measure and control humidity at temperatures below 0° C.

To those skilled in the art, many modifications and variations of the present invention ar possible in light of the above teachings. It is therefore to be understood that the present invention can be practiced otherwise than as specifically described herein and still will be within the spirit and scope of the appended claims.

We claim:

1. A dew point sensor comprising:
    a hollow cylindrical housing;
    a mirrored surface disposed on the interior surface of said hollow cylindrical housing;
    means for establishing a temperature gradient along the mirrored surface thereby creating condensation of water vapor on only a portion of the mirrored surface;
    means for scanning the mirrored surface and for detecting the edge of said condensation next to the area of the mirrored surface free from condensation;
    means for determining the temperature at the edge of said condensation which represents the dew point temperature.

2. The sensor of claim 1 wherein the means for scanning the mirrored surface and for detecting the edge of said condensation comprises:
    a light source directed toward the mirrored surface;
    a photodetecting means for detecting reflected light from the mirrored surface;
    means interposed between the light source and the photodetecting means for masking the light directed toward the mirrored surface into a plurality of distinct light and dark areas thereby enabling the photodetecting means to detect the edge of said condensation.

3. The senor of claim 2 wherein the means for detecting the edge of said condensation further comprises:
    a servo motor having a shaft for mounting the photodetecting means and the light source; and
    condition sensing means having its input connected to the photodetecting means and its output connected to the servo motor for rotating the shaft to a position wherein the photodetecting means detects the edge of said condensation.

4. The sensor of claim 2 wherein the masking means comprises a light mask having areas which are transparent and opaque for defining a symmetrical pattern having a plurality of transparent regions, the photodetecting means having individual sections for respectively detecting the reflected light condition of each region.

5. The sensor of claim 3 together with means for measuring the angular position of the shaft;
    means for varying the temperature gradient along the mirrored surface until the edge of said condensation appears at the median point along the length of the mirrored surface; and
    means located at the median point for measuring the temperature thereat.

6. The sensor of claim 3 wherein the masking means comprises a light mask having areas which are transparent and opaque for defining a symmetrical pattern having a plurality of transparent regions, the photodetecting means having individual sections for respectively detecting the reflected light condition of each region;
    means for measuring the angular position of the shaft;
    means for varying the temperature gradient along the mirrored surface until the edge of said condensation image appears at the median point along the length of the mirrored surface; and
    means located at the median point for measuring the temperature thereat.

7. A method for measuring dew point temperature of an environment comprising the steps of:
    subjecting a mirrored surface disposed on the interior surface of a hollow cylindrical housing to an environment where humidity is present;
    establishing a temperature gradient along the mirrored surface thereby creating condensation of water vapor on only a portion of the mirrored surface;

scanning the mirrored surface to detect the edge of said condensation next to the area of the mirrored surface that is free from condensation;

measuring the temperature at the edge of said condensation which represents the dew point temperature.

8. The method of claim 7 wherein detecting the edge of said condensation comprises the steps of:

masking light reflected from the mirrored surface into a symmetrical pattern of light-transparent area; and sensing preselected maximum and minimum light conditions in the respective areas.

9. The method set forth in claim 8 together with the step of varying the gradient until the edge of the condensation coincides with a median point along the length of the mirrored surface.

10. The method set forth in claim 8 wherein the masking and sensing of light further comprises the step of scanning the mirrored surface with a masked light source coupled to a photodetector.